US009885348B2

(12) United States Patent
Suzuki (10) Patent No.: US 9,885,348 B2
(45) Date of Patent: *Feb. 6, 2018

(54) RECIPROCATION PUMP AND A DIALYSIS APPARATUS EQUIPPED WITH THE RECIPROCATION PUMP

(75) Inventor: Hiroaki Suzuki, Makinohara (JP)

(73) Assignee: Nikkiso Company Limited, Tokyo (JP)

( * ) Notice: Subject to any disclaimer, the term of this patent is extended or adjusted under 35 U.S.C. 154(b) by 546 days.

This patent is subject to a terminal disclaimer.

(21) Appl. No.: 13/479,687

(22) Filed: May 24, 2012

(65) Prior Publication Data

US 2012/0266749 A1  Oct. 25, 2012

Related U.S. Application Data

(63) Continuation of application No. PCT/JP2010/070826, filed on Nov. 22, 2010.

(30) Foreign Application Priority Data

Nov. 24, 2009 (JP) ................. 2009-266395

(51) Int. Cl.
F04B 23/06 (2006.01)
A61M 1/16 (2006.01)
(Continued)

(52) U.S. Cl.
CPC .............. *F04B 23/06* (2013.01); *A61M 1/14* (2013.01); *A61M 1/1639* (2014.02);
(Continued)

(58) Field of Classification Search
CPC ............... F04B 25/005; F04B 27/0423; F04B 27/0478; F04B 43/02; F04B 43/025;
(Continued)

(56) References Cited

U.S. PATENT DOCUMENTS 3,288,036 A * 11/1966 Fisher ................. F15B 11/0365
92/129
4,178,240 A  12/1979 Pinkerton
(Continued)

FOREIGN PATENT DOCUMENTS

DE   2408119   8/1974
JP   50-24675   3/1975
(Continued)

*Primary Examiner* — Bryan Lettman
*Assistant Examiner* — Charles W Nichols
(74) *Attorney, Agent, or Firm* — Harness, Dickey & Pierce, P.L.C.

(57) ABSTRACT

A reciprocation pump has a supply liquid-side sub-pumping chamber arranged adjacent to the supply liquid-side pumping chamber at an external side. A waste liquid-side sub-pumping chamber is arranged adjacent to the waste liquid-side pumping chamber at an external side. A rod extends through the supply liquid-side sub-pumping chamber, the supply liquid-side pumping chamber, the waste liquid-side pumping chamber and the waste liquid-side sub-pumping chamber. The rod is connected to the reciprocation mechanism and the driving source to transmit a driving force of the driving source to the reciprocation mechanism. Sealing members are arranged, respectively, in walls through which the rod extends to partition the supply liquid-side pumping chamber and the supply liquid-side sub-pumping chamber as well as the waste liquid-side pumping chamber and the waste liquid-side sub-pumping chamber.

8 Claims, 7 Drawing Sheets

(51) Int. Cl.
*A61M 1/14* (2006.01)
*F04B 3/00* (2006.01)
*F04B 9/02* (2006.01)
*F04B 43/02* (2006.01)
*F04B 53/02* (2006.01)
*F04B 13/02* (2006.01)

(52) U.S. Cl.
CPC ............ *A61M 1/1641* (2014.02); *F04B 3/00* (2013.01); *F04B 9/02* (2013.01); *F04B 13/02* (2013.01); *F04B 43/023* (2013.01); *F04B 53/02* (2013.01)

(58) Field of Classification Search
CPC .... F04B 43/026; F04B 45/043; F04B 45/047; F04B 3/00; F04B 9/02; F04B 13/02; F04B 23/06; F04B 43/023; F04B 53/02; A61M 1/14; A61M 1/1639; A61M 1/1641
USPC ......... 417/244, 250, 251, 267, 410.1, 413.1; 210/646; 92/48, 146, 151
See application file for complete search history.

(56) References Cited

U.S. PATENT DOCUMENTS

| | | | | |
|---|---|---|---|---|
| 4,197,196 | A | * | 4/1980 | Pinkerton ........... A61M 1/1656 210/321.65 |
| 4,676,905 | A | * | 6/1987 | Nagao et al. ................. 210/646 |
| 4,761,118 | A | * | 8/1988 | Zanarini ....................... 417/254 |
| 4,778,356 | A | | 10/1988 | Hicks |
| 4,857,199 | A | * | 8/1989 | Cortial .................... A61M 1/16 210/101 |
| 5,279,504 | A | * | 1/1994 | Williams ...................... 417/393 |
| 2005/0254971 | A1 | * | 11/2005 | Ohya et al. ................. 417/413.1 |

FOREIGN PATENT DOCUMENTS

| | | |
|---|---|---|
| JP | 64-008367 | 1/1989 |
| JP | 10-299642 | 11/1998 |
| JP | 2003-284772 | 10/2003 |

* cited by examiner

RECIPROCATION PUMP AND A DIALYSIS APPARATUS EQUIPPED WITH THE RECIPROCATION PUMP

CROSS-REFERENCE TO RELATED APPLICATIONS

This application is a continuation of International Application No. PCT/JP2010/070826, filed Nov. 22, 2010, which claims priority to Japanese Application No. 2009-266395, filed Nov. 24, 2009. The disclosures of the above applications are incorporated herein by reference.

FIELD

The present disclosure relates to a reciprocation pump with a supply liquid-side pumping chamber to supply liquid to an objective apparatus and a waste liquid-side pumping chamber to discharge waste liquid from the objective apparatus to the outside, and to a dialysis apparatus equipped with the reciprocation pump.

BACKGROUND

In general, a blood purification apparatus such as a dialyzer is used in hemodialysis treatment. A dialysate supplying line, to supply the dialysate, as well as a dialysate discharge line, to discharge the waste dialysate, is connected to the blood purification apparatus. The dialysate supply line and dialysate discharge line extend from a dialysis apparatus main body and are connected to the blood purification apparatus to supply the dialysate to the blood purification apparatus and to discharge the waste dialysate from the blood purification apparatus to the outside.

Figure 6:
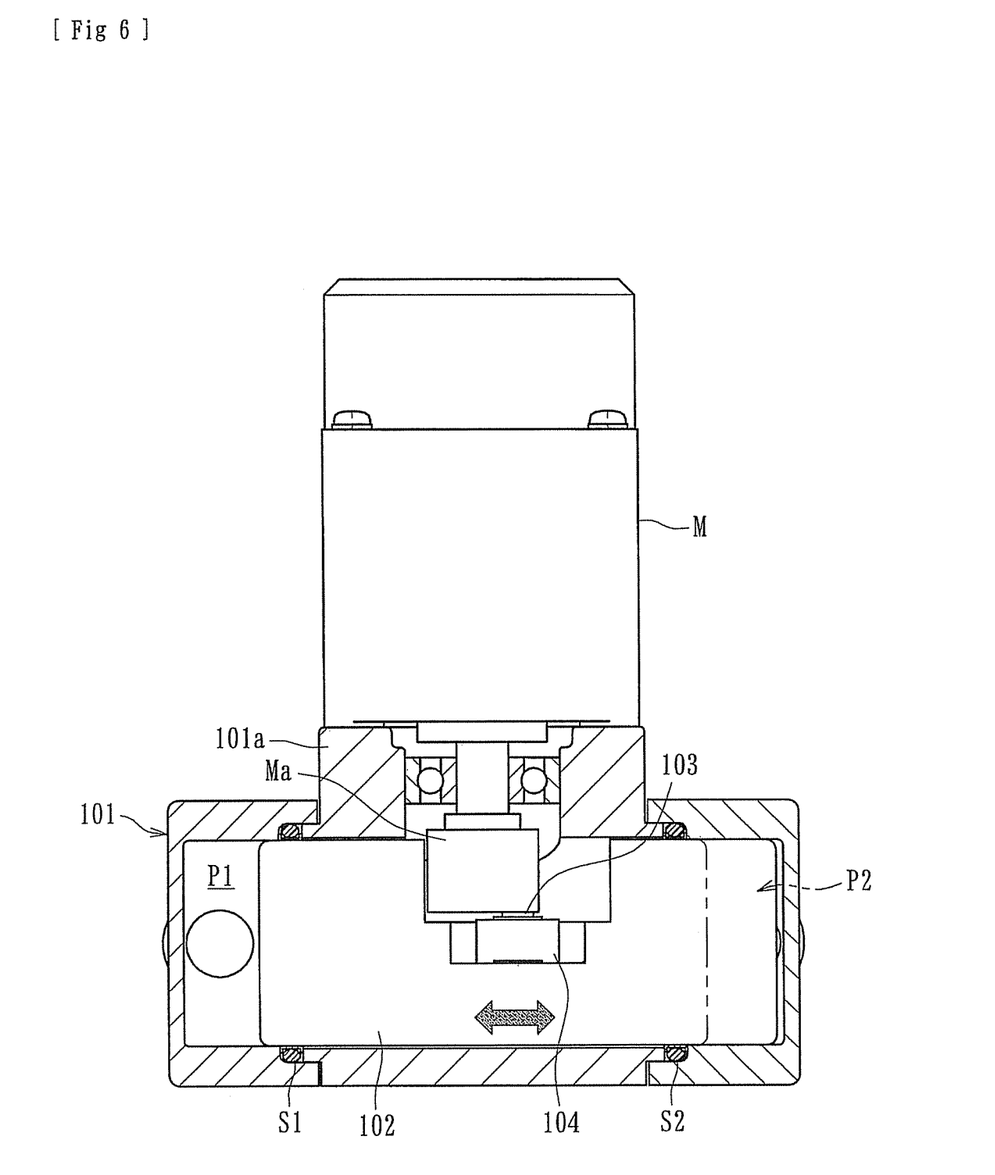
FIG. 6 is a longitudinal section plan view of a prior art reciprocation pump.
Figure 7:
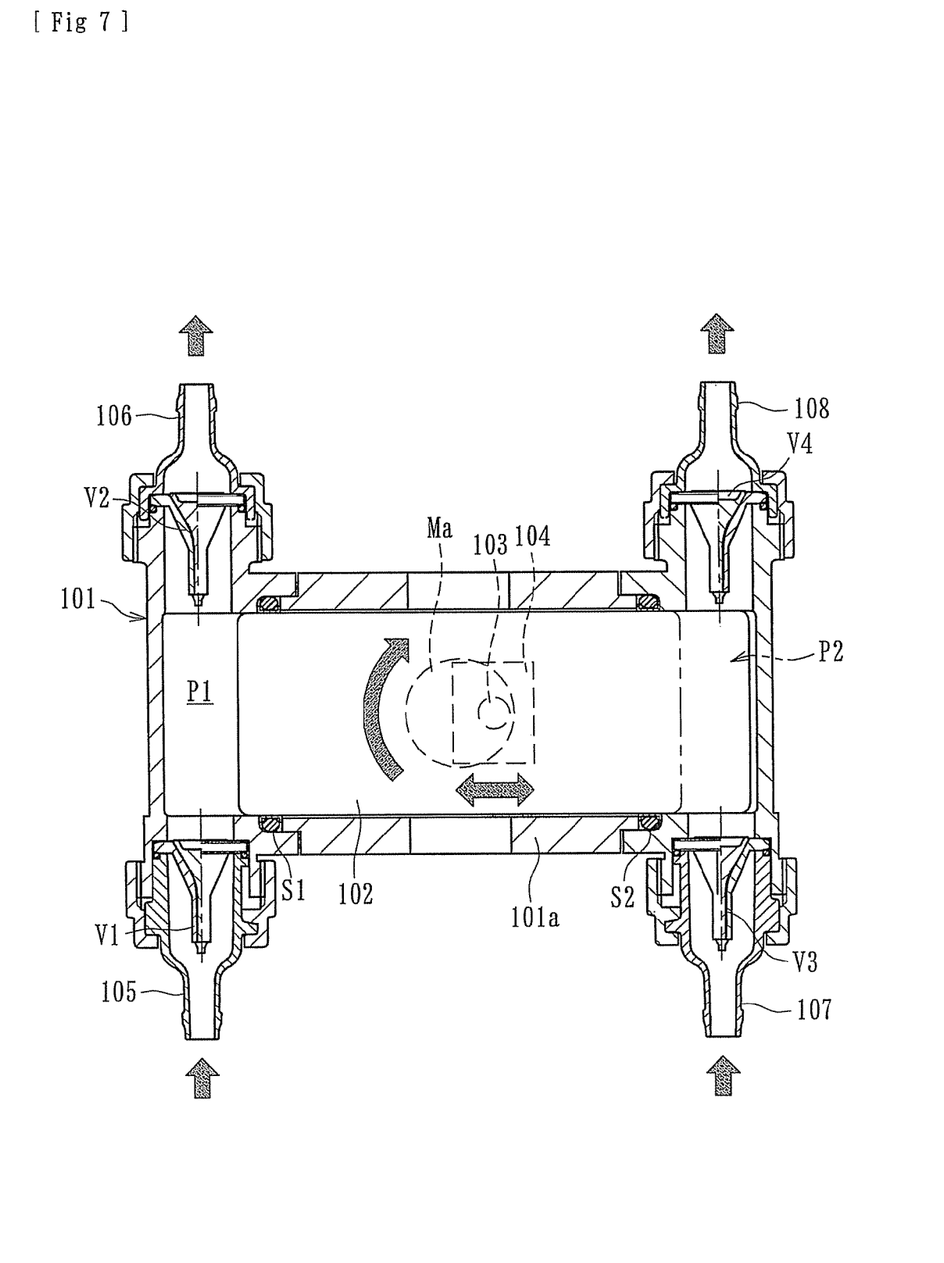
FIG. 7 is a longitudinal section side elevation view of a prior art reciprocation pump.

The reciprocation pump (duplex pump) is connected to the dialysis apparatus main body across the dialysate supply line and the dialysate discharge line. As shown in FIGS. 6 and 7, the reciprocation pump includes a casing 101 that reciprocatably accommodates a plunger 102. A supply liquid-side pumping chamber P1 and a waste liquid-side pumping chamber P2 are formed by the plunger 102 within the casing 101. Supply liquid-side ports 105, 106 communicate with the supply liquid-side pumping chamber P1. Waste liquid-side ports 107, 108 communicate with the waste liquid-side pumping chamber P2. A motor M reciprocates the plunger 102.

The supply liquid-side ports 105, 106 are provided with check valves V1, V2, respectively. The waste liquid-side ports 107, 108 are also provided with check valves V3, V4, respectively. The reciprocation pump is structured so that the supply liquid-side pumping chamber P1 sucks the liquid (dialysate) from its source through the supply liquid-side port 105. The chamber P1 supplies the dialysate to a blood purification apparatus (not shown in FIGS. 6 and 7) through the supply liquid-side port 106. The waste liquid-side pumping chamber P2 receives the waste liquid (waste dialysate) from the blood purification apparatus through the waste liquid-side port 107 and discharges it through the waste liquid-side port 108 to the outside.

An eccentric cam 103 is mounted on an output shaft Ma of the motor M. A block 104, reciprocated by the eccentric cam 103, is mounted on the plunger 102. With the motor M driving, the plunger 102 can be reciprocated via the block 104. The supply and discharge of the dialysate can be performed as described above. Such a reciprocation pump is disclosed in Japanese Laid-open Patent Publication No. 2003-284772.

However, in such a prior art reciprocation pump, shown in FIGS. 6 and 7, it requires a motor casing 101a for mounting the motor Mon the pump casing 101. Also, it requires sealing members S1, S2 interposed between the motor casing 101a and the pump casing 101. Thus, it is believed that the dialysate to be supplied to the blood purification apparatus and the waste dialysate would leak to the outside of the reciprocation pump due to aged degradation of the sealing members S1, S2. Such a problem is also found in reciprocal pumps in other fields that supply liquids to objective apparatus other than blood purification apparatus.

SUMMARY

It is, therefore, an object of the present disclosure to provide a reciprocation pump that can prevent a liquid, to be supplied to an objective apparatus, and a waste liquid, to be discharged from the objective apparatus, from leaking outside of the reciprocation pump as well as a dialysis apparatus equipped with the reciprocation pump.

To achieve the above mentioned object, a reciprocation pump comprises a supply liquid-side pumping chamber and a waste liquid side pumping chamber. The supply liquid-side pumping chamber supplies a liquid from a source to an objective apparatus. The waste liquid-side pumping chamber discharges a waste liquid from the objective apparatus to the outside. A reciprocation mechanism reciprocates between the supply liquid-side pumping chamber and the waste liquid-side pumping chamber. The reciprocating motion of the reciprocation mechanism performs the suction and discharge of the liquid to and from the supply liquid-side pumping chamber as well as the suction and discharge of the waste liquid to and from the waste liquid-side pumping chamber. A driving source drives the reciprocation mechanism. The reciprocation pump, via the supply liquid-side pumping chamber, supplies the liquid from the source to the objective apparatus. The waste liquid is discharged from the objective apparatus, via the waste liquid-side pumping chamber, to the outside. A supply liquid-side sub-pumping chamber is arranged adjacent to the supply liquid-side pumping chamber at the external side. A waste liquid-side sub-pumping chamber is arranged adjacent to the waste liquid-side pumping chamber at the external side. A rod extends through the supply liquid-side sub-pumping chamber, the supply liquid-side pumping chamber, the waste liquid-side pumping chamber and the waste liquid-side sub-pumping chamber. The rod is connected to the reciprocation mechanism and the driving source to transmit a driving force from the driving source to the reciprocation mechanism. Sealing mechanisms are arranged, respectively, in walls through which the rod extends to partition the supply liquid-side pumping chamber and the supply liquid-side sub-pumping chamber as well as the waste liquid-side pumping chamber and the waste liquid-side sub-pumping chamber.

The reciprocation pump further includes diaphragms, respectively, mounted on the distal end and the proximal end of the rod to form the supply liquid-side sub-pumping chamber and the waste liquid-side sub-pumping chamber, respectively.

The liquid is supplied to the objective apparatus through both the supply liquid-side pumping chamber and the supply liquid-side sub-pumping chamber. Waste liquid is discharged to the outside through both the waste liquid-side pumping chamber and the waste liquid-side sub-pumping chamber.

The reciprocation mechanism includes a plunger formed on the rod. The plunger, along with the casing, forms the supply liquid-side pumping chamber and the waste liquid-side pumping chamber. A central sealing member is arranged between the supply liquid-side pumping chamber and the waste liquid-side pumping chamber at a substantially reciprocating center of the plunger. The sealing member seals the supply liquid-side pumping chamber from the waste liquid-side pumping chamber.

The reciprocation mechanism includes a diaphragm mounted on the rod. The diaphragm, along with the casing, forms the supply liquid-side pumping chamber and the waste liquid-side pumping chamber, respectively.

The objective apparatus is a blood purification apparatus. The liquid is dialysate.

The present disclosure also provides a dialysis apparatus equipped with the above reciprocation pump.

The supply liquid-side sub-pumping chamber and the waste liquid-side sub-pumping chamber are arranged at the external sides, respectively, of the supply liquid-side pumping chamber and the waste liquid-side pumping chamber. The sealing members are arranged, respectively, in walls to partition the supply liquid-side pumping chamber and the supply liquid-side sub-pumping chamber as well as the waste liquid-side pumping chamber and the waste liquid-side sub-pumping chamber. Thus, this makes it possible to keep constant volumes in the supply liquid-side pumping chamber and the waste liquid-side pumping chamber. In addition, this makes it possible to prevent the liquid (dialysate) from leaking to the outside. The liquid flows into the sub-pumping chambers respectively of the supply liquid-side pumping chamber and the waste liquid-side pumping chamber even if any leakage of the liquid is caused by aged degradation of the sealing members.

The reciprocation pump further comprises diaphragms respectively mounted on the distal end and the proximal end of the rod. The diaphragms, with the casing, form the supply liquid-side sub-pumping chamber and the waste liquid-side sub-pumping chamber, respectively. Thus, it is possible to eliminate the necessity to separate sealing members at the mounting portions of the diaphragms.

The liquid is supplied to the objective apparatus through both the supply liquid-side pumping chamber and the supply liquid-side sub-pumping chamber. Waste liquid is discharged to the outside through both the waste liquid-side pumping chamber and the waste liquid-side sub-pumping chamber. Thus, it is possible to supply leaked liquid to the objective apparatus through the supply liquid-side sub-pumping chamber if the liquid leaks from the supply liquid-side pumping chamber to the supply liquid-side sub-pumping chamber due to aged degradation of the sealing member. Similarly, it is possible to discharge leaked waste liquid from the waste liquid-side sub-pumping chamber to the outside if the waste liquid leaks from the waste liquid-side pumping chamber to the waste liquid-side sub-pumping chamber.

The central sealing member is arranged between the supply liquid-side pumping chamber and the waste liquid-side pumping chamber. The central sealing member is positioned substantially at the reciprocating center of the plunger to seal the supply liquid-side pumping chamber and the waste liquid-side pumping chamber from each other. Leaked liquid can flow from the supply liquid-side pumping chamber to the waste liquid-side pumping chamber. Leaked waste liquid can flow from the waste liquid-side pumping chamber to the supply liquid-side pumping chamber. Thus, it is possible to prevent leaked liquid and leaked waste liquid from leaking to the outside of the reciprocation pump.

The reciprocation mechanism comprises a diaphragm mounted on the rod. The diaphragm and casing form the supply liquid-side pumping chamber and the waste liquid-side pumping chamber. Thus, it is possible to eliminate any type of sealing member between the supply liquid-side pumping chamber and the waste liquid-side pumping chamber as compared with a pump using a plunger for this purpose.

The objective apparatus is a blood purification apparatus. The liquid is dialysate. Thus, it is possible to prevent the dialysate or the waste dialysate from leaking to the outside of the reciprocation pump.

Additionally, it is possible to provide a dialysis apparatus having superior effects with the defined reciprocation pump.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Embodiments of the present disclosure will be described with reference to the accompanied drawings.

Figure 1:
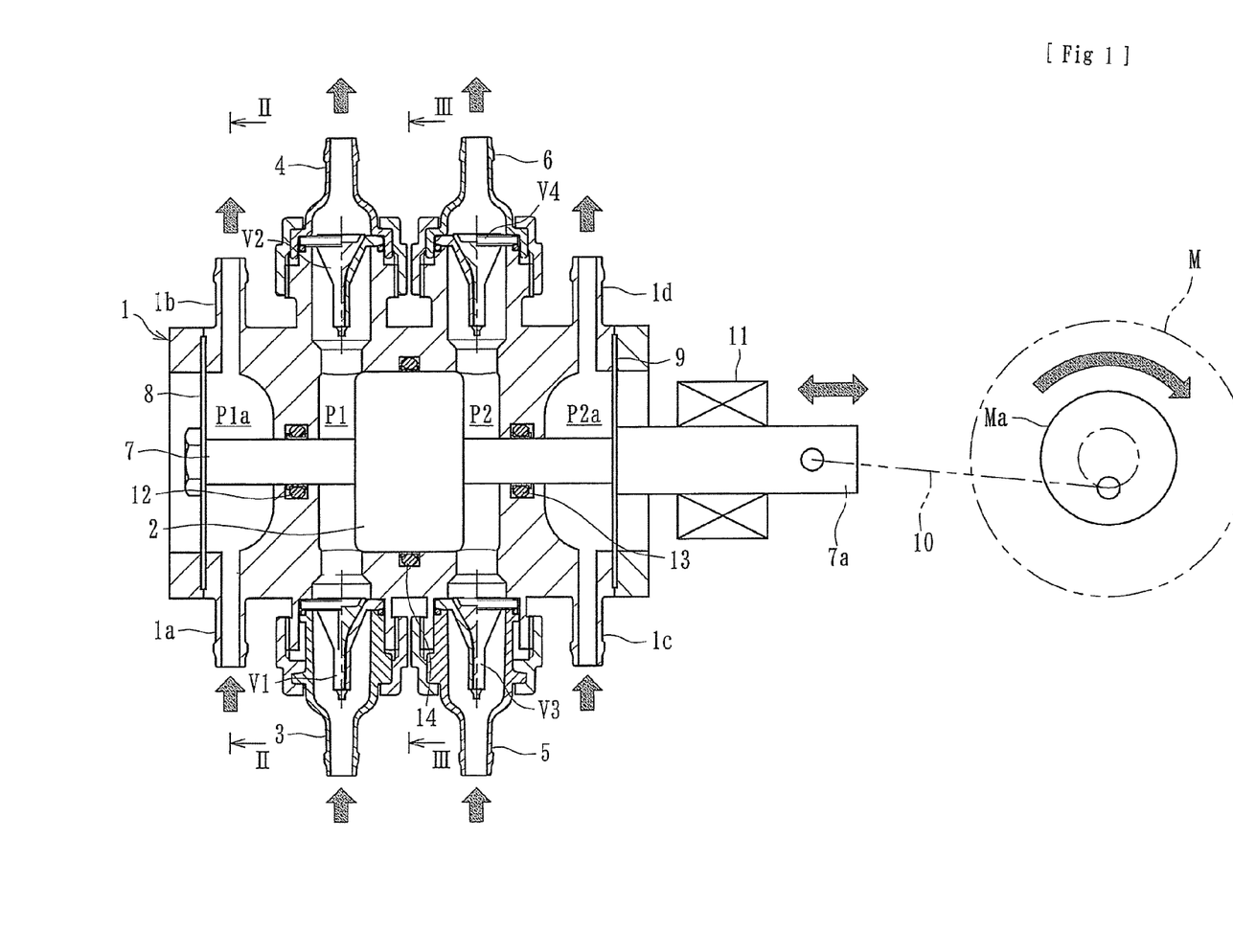
FIG. 1 is a longitudinal-section view of a reciprocation pump of the present disclosure.
Figure 2:
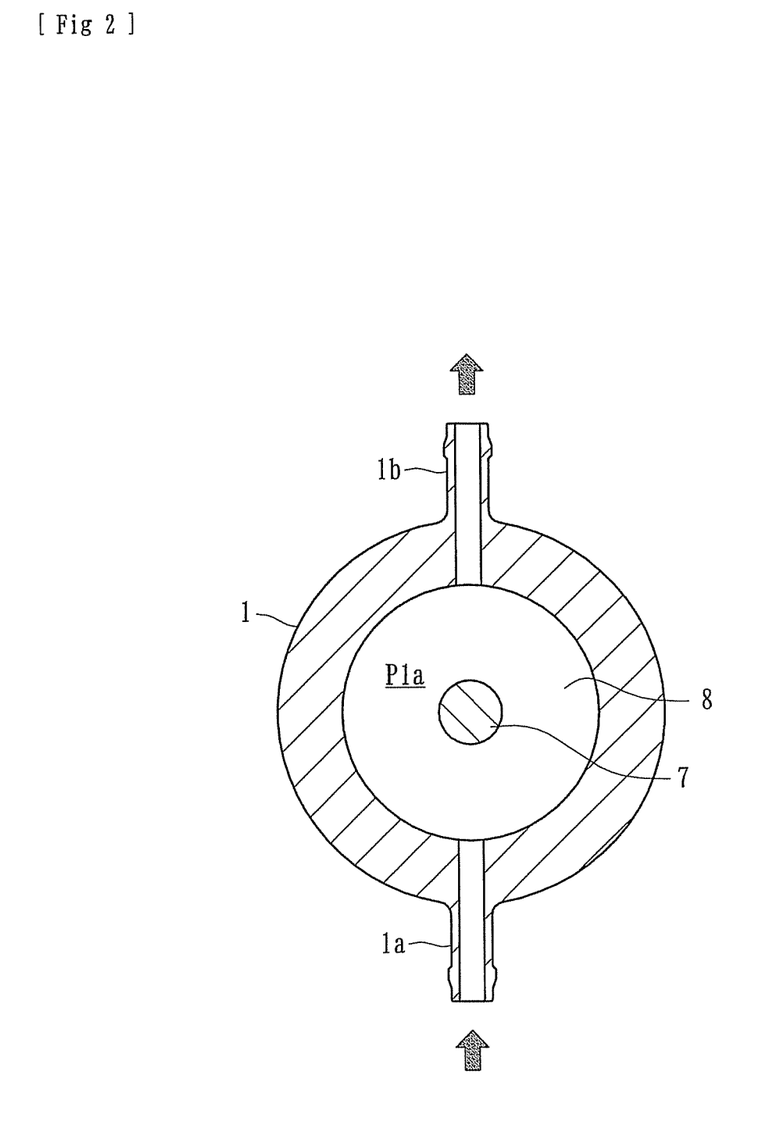
FIG. 2 is a cross-sectional view taken along a line II-II of FIG. 1.
Figure 3:
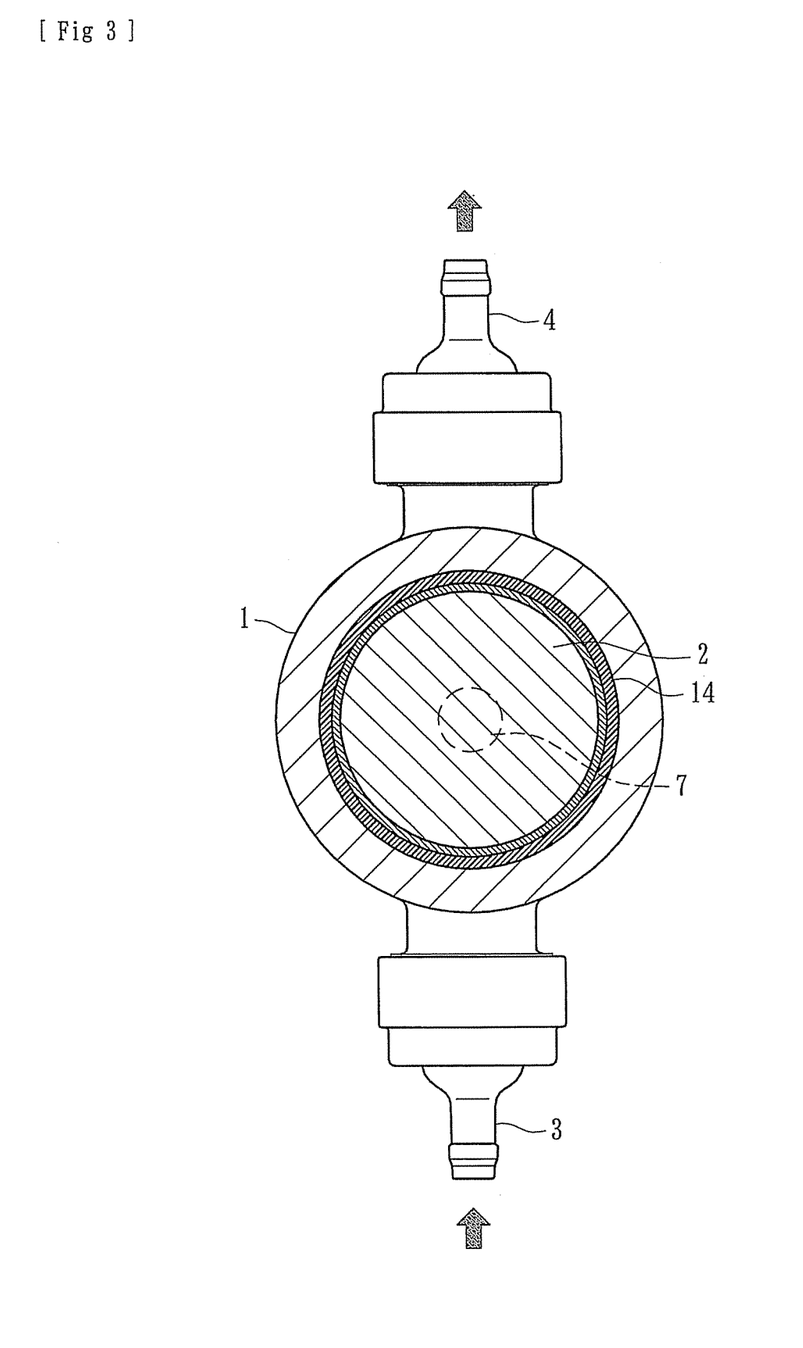
FIG. 3 is a cross-sectional view taken along a line of FIG. 1.

The reciprocation pump of one embodiment of the present disclosure can be applied to a hemodialysis apparatus. The reciprocation pump includes a so-called duplex pump, with a supply liquid-side pumping chamber, to supply a liquid to an objective apparatus (e.g. blood purification apparatus). A waste liquid is discharged from the objective apparatus to a waste liquid-side pumping chamber. As shown in FIGS. 1-3, the reciprocation pump of the present disclosure mainly includes a casing 1 where a supply liquid-side pumping chamber P1 and a waste liquid-side pumping chamber P2 are formed. A plunger 2 acts as a reciprocation mechanism. A supply liquid-side sub-pumping chamber P1*a* is formed by a diaphragm 8 and the casing 1. A waste liquid-side sub-pumping chamber P2*a* formed by a diaphragm 9 and the casing 1. A rod 7 and motor M acts as a driving source. Sealing members 12, 13, and a central sealing member 14 seal the chambers.

Figure 4:
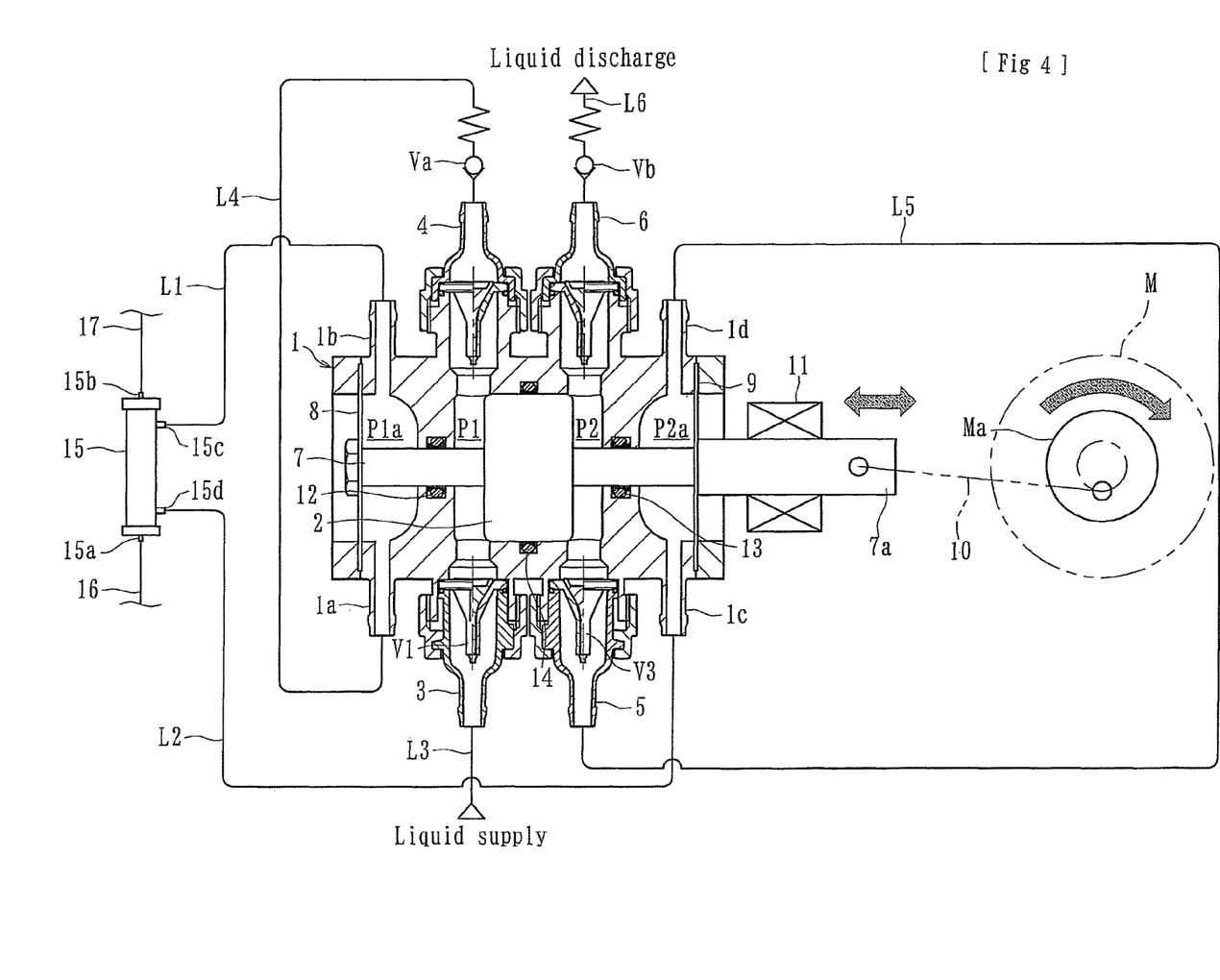
FIG. 4 is a schematic cross-sectional view showing a connection between the reciprocation pump and a blood purification apparatus.

As shown in FIG. 4, the reciprocation pump is connected to a blood purification apparatus 15 acting as the objective apparatus. The blood purification apparatus 15 is formed with a blood inlet port 15*a*, a blood outlet port 15*b*, dialysate inlet port 15c, and dialysate outlet port 15d. An arterial blood circuit 16 is connected to the blood inlet port 15a. A venous blood circuit 17 is connected to the blood outlet port 15b. In addition, a dialysate supply line L1, extending from the reciprocation pump, is connected to a dialysate inlet port 15c. A dialysate discharging line L2, extending from the reciprocation pump, is connected to a dialysate outlet port 15d.

The arterial blood circuit 16 and the venous blood circuit 17 form a blood circuit to extracorporeally circulate a patient's blood. They are respectively equipped with an arterial puncture needle and a venous puncture needle (not shown). The blood purification apparatus 15 contains an enormous number of hollow fiber membranes (blood purification membranes). The inside of each hollow fiber membrane communicates with the blood inlet port 15a and the blood outlet port 15b and forms a blood flow route. On the other hand, a space between the outer circumferential surface of each hollow fiber membrane and the inner circumferential surface of the casing of the blood purification apparatus 15 communicates with the dialysate inlet port 15c and the dialysate outlet port 15d to form the dialysate flow route. The route passes the dialysate (liquid) supplied by the reciprocation pump. Since the hollow fiber membrane is formed with an enormous number of micro pores, unnecessary materials (blood waste materials) can be removed by the dialysate via the hollow fiber membranes.

The casing 1 of the reciprocation pump is formed from metallic parts or molded hard plastic parts. The casing forms the supply liquid-side pumping chamber P1, the waste liquid-side pumping chamber P2, the supply liquid-side sub-pumping chamber P1a, and the waste liquid-side sub-pumping chamber P2a. Projected connection ports 1a, 1b are formed on the casing 1 at the bottom and top of the supply liquid-side sub-pumping chamber P1a. Appropriate flow routes (e.g. flexible tubes) can be connected to the connection ports. Similarly, projected connection ports 1c, 1d are formed on the casing 1 at the bottom and top of the waste liquid-side sub-pumping chamber P2a. Appropriate flow routes (e.g. flexible tubes) can be connected connection ports 1c, 1d.

The supply liquid-side pumping chamber P1 supplies the dialysate to the blood purification apparatus 15 (FIG. 4). A supply liquid-side inlet port 3 and a supply liquid-side outlet port 4 are arranged at the bottom and top of the supply liquid-side pumping chamber P1. Reference characters V1, V2 denote check valves that are mounted, respectively, on the supply liquid-side inlet port 3 and the supply liquid-side outlet port 4. The valves V1, V2 act to permit flow of the dialysate from the bottom to the top and prevent flow of the dialysate from the top to the bottom of the supply liquid-side pumping chamber P1.

The waste liquid-side pumping chamber P2 discharges a waste liquid (waste dialysate) to the outside of the reciprocation pump. A waste liquid-side inlet port 5 and a waste liquid-side outlet port 6 are arranged at the bottom and top of the waste liquid-side pumping chamber P2. Reference characters V3, V4 denote check valves that are mounted, respectively, on the waste liquid-side inlet port 5 and the waste liquid-side outlet port 6. The valves V3, V4 act to permit flow of the waste liquid from the bottom to the top and prevent flow of the waste liquid from the top to the bottom of the waste liquid-side pumping chamber P2.

The plunger 2 reciprocates between the supply liquid-side pumping chamber P1 and the waste liquid-side pumping chamber P2. The motor M is a driving source. The plunger performs the suction and discharge of the dialysate to and from the supply liquid-side pumping chamber P1 and the suction and discharge of the waste dialysate to and from the waste liquid-side pumping chamber P2. The suction of the dialysate from its source and the supply of the dialysate to the blood purification apparatus 15 are repeatingly performed in the supply liquid-side pumping chamber P1. The suction of the waste dialysate from the blood purification apparatus 15 and the discharge of the waste dialysate to the outside of the reciprocation pump are repeatingly performed in the waste liquid-side pumping chamber P2. Simultaneously and repeatingly suction is performed in the waste liquid-side pumping chamber P2 during reciprocal motion of the plunger 2.

The supply liquid-side sub-pumping chamber P1a is arranged adjacent to the supply liquid-side pumping chamber P1 at an external side (left-side). The supply liquid-side sub-pumping chamber P1a is formed by the casing 1 and diaphragm 8, mounted on the rod 7. The diaphragm 8 is adapted to perform the suction and discharge of the dialysate via the connection ports 1a, 1b. The diaphragm 8 is secured to the casing 1 by its peripheral edge fit into the casing 1 via a sealed manner. The diaphragm 8 is adapted to be displaced by the rod 7 to vary the volume of the supply liquid-side sub-pumping chamber P1a.

The waste liquid-side sub-pumping chamber P2a is arranged adjacent to the waste liquid-side pumping chamber P2 at an external side (right-side). The waste liquid-side sub-pumping chamber P2a is formed by the casing 1 and diaphragm 9, mounted on the rod 7. The diaphragm 9 is adapted to perform the suction and discharge of the waste dialysate via the connection ports 1c, 1d. The diaphragm 9 is secured to the casing 1 by its peripheral edge fit into the casing 1, via a sealed manner. The diaphragm 9 is adapted to be displaced by the rod 7 to vary the volume of the waste liquid-side sub-pumping chamber P2a.

The rod 7 extends through the supply liquid-side sub-pumping chamber P1a, the supply liquid-side pumping chamber P1, the waste liquid-side pumping chamber P2 and the waste liquid-side sub-pumping chamber P2a. The rod 7 is connected to the plunger 2 (reciprocation mechanism) and the motor M (driving source) to transmit a driving force of the motor M to the plunger 2 to reciprocate the plunger 2. More particularly, diaphragms 8, 9 are mounted, respectively, on the distal end and the proximal end of the rod 7. The plunger 2 is also mounted on the rod 7 at a substantially central portion between the diaphragms 8, 9.

The supply liquid-side sub-pumping chamber P1a communicates with the supply liquid-side pumping chamber P1 so that it permits flow of the dialysate. The diaphragm 8 is interlocked with the plunger 2 and varies the volume of the supply liquid-side sub-pumping chamber P1a reversely to the volume variation of the supply liquid-side pumping chamber P1. The volume of the supply liquid-side sub-pumping chamber P1a is reduced in accordance with an increase of the volume of the supply liquid-side pumping chamber P1. To the contrary, the volume of the supply liquid-side sub-pumping chamber P1a is increased in accordance with a reduction of the volume of the supply liquid-side pumping chamber P1. Similarly, the waste liquid-side sub-pumping chamber P2a communicates with the waste liquid-side pumping chamber P2 so that it permits flow of the waste dialysate. The diaphragm 9 is interlocked with the plunger 2 and varies the volume of the waste liquid-side sub-pumping chamber P2a reversely to the volume variation of the waste liquid-side pumping chamber P2. The volume of the waste liquid-side sub-pumping chamber P2a is reduced in accordance with an increase of the volume of the waste liquid-side pumping chamber P2. To the contrary, the volume of the waste liquid-side sub-pumping chamber P2a is increased in accordance with reduction of the volume of the waste liquid-side pumping chamber P2.

As shown in FIG. 1, a crosshead 7a is mounted on the proximal end of the rod 7. The crosshead 7a is received through a crosshead cylinder 11 to guide the reciprocal motion of the rod 7. An output shaft Ma of the motor M is connected to the crosshead 7a, via a connecting rod 10. Thus, the rod 7 is reciprocated by the rotation of the motor M, via the connecting rod 10.

Sealing members 12, 13 include sealing parts in common use, such as O-rings, arranged, respectively, in walls through which the rod 7 extends. The sealing members 12, 13 partition the supply liquid-side pumping chamber P1 and the supply liquid-side sub-pumping chamber P1a as well as the waste liquid-side pumping chamber P2 and the waste liquid-side sub-pumping chamber P2a. The sealing members 12, 13 enable reciprocal sliding motion of the rod 7. Also, the sealing members 12, 13 prevent leakage of the liquid (dialysate) between the supply liquid-side pumping chamber P1 and the supply liquid-side sub-pumping chamber P1a as well as the waste liquid-side pumping chamber P2 and the waste liquid-side sub-pumping chamber P2a.

A central sealing member 14 also includes a sealing part in common use, such as an O-ring, arranged between the supply liquid-side pumping chamber P1 and the waste liquid-side pumping chamber P2. The central sealing member 14 is positioned substantially at a reciprocating center of the plunger 2 to seal the supply liquid-side pumping chamber P1 from the waste liquid-side pumping chamber P2. The supply liquid-side pumping chamber P1 is sealed by the sealing member 12 and the central sealing member 14. The waste liquid-side pumping chamber P2 is sealed by the sealing member 13 and the central sealing member 14.

The dialysate is supplied to the blood purification apparatus 15 via both the supply liquid-side pumping chamber P1 and the supply liquid-side sub-pumping chamber P1a. The waste dialysate is discharged from the blood purification apparatus 15 via both the waste liquid-side pumping chamber P2 and the waste liquid-side sub-pumping chamber P2a. More particularly, as shown in FIG. 4, the dialysate supplying line L1 is connected between the dialysate inlet port 15c of the blood purification apparatus 15, and the projected connection port 1b. The dialysate discharging line L2 is connected between the dialysate discharging port 15d, of the blood purification apparatus 15, and the projected connection port 1c.

A flow route L4, forming part of the dialysate supply line L1, is connected between the projected-connection port 1a and the supply liquid-side outlet port 4. The supply liquid-side inlet port 3 is connected to a flow route L3, forming part of the dialysate supplying line L1. The flow route L3 is further connected to the supply source (not shown) of the dialysate, conditioned to a predetermined concentration. Thus, the dialysate fed from the supply source can be supplied to the blood purification apparatus 15 through the supply liquid-side pumping chamber P1 and the supply liquid-side sub-pumping chamber P1a.

On the other hand, a flow route L5, forming part of the dialysate discharging line L2, is connected to the projected connection port 1d and the waste liquid-side inlet port 5. The waste liquid-side outlet port 6 is connected to a flow route L6, forming part of the dialysate discharging line L2. The flow route L6 is connected to any discharged liquid recovering mechanism (not shown). Thus, the liquid discharged from the blood purification apparatus 15 can be recovered by the discharged liquid recovering mechanism through the waste liquid-side sub-pumping chamber P2a and the waste liquid-side pumping chamber P2. Reference characters Va, Vb in FIG. 4 denotes back pressure valves connected respectively to the flow route L4, L6.

When the plunger 2 is moved, by the motor M, toward the right in FIG. 4, the dialysate is sucked into the supply liquid-side pumping chamber P1 from the dialysate supplying source. Simultaneously, the diaphragm 8 is also pulled and thus deflected toward the right. This reduces the volume of the supply liquid-side sub-pumping chamber P1a. Thus, the dialysate is supplied to the blood purification apparatus 15 from the supply liquid-side sub-pumping chamber P1a, via the dialysate supplying line L1. On the other hand, when the plunger 2 is moved, by the motor M, toward the left in FIG. 4, the dialysate is supplied to the blood purification apparatus 15 from the supply liquid-side pumping chamber P1. Simultaneously, the diaphragm 8 is also pushed and thus deflected toward the left. This increases the volume of the supply liquid-side sub-pumping chamber P1a. Thus, part of the dialysate supplied to the blood purification apparatus 15 is absorbed or supplemented by the supply liquid-side sub-pumping chamber P1a.

If the discharging capacities of the supply liquid-side pumping chamber P1 and the waste liquid-side pumping chamber P2 are set about twice those of the supply liquid-side sub-pumping chamber P1a and the waste liquid-side sub-pumping chamber P2a, the pulsation, caused during the dialysate supplied to the blood purification apparatus 15 from the reciprocation pump, can be reduced. In this case the pulsation will be reduced if the discharging capacities of the supply liquid-side pumping chamber P1 and the waste liquid-side pumping chamber P2 are set larger than those of the supply liquid-side sub-pumping chamber P1a and the waste liquid-side sub-pumping chamber P2a.

Other connecting arrangement between the reciprocation pump and the blood purification apparatus 15 other than that shown and described with reference to FIG. 4, can be adopted if the dialysate is supplied to the blood purification apparatus 15 via both the supply liquid-side pumping chamber P1 and the supply liquid-side sub-pumping chamber P1a. The waste dialysate is discharged from the blood purification apparatus 15 via both the waste liquid-side pumping chamber P2 and the waste liquid-side sub-pumping chamber P2a. For example, it is possible to suck the dialysate from the supply source, via the projected connection port 1a and discharge the waste dialysate, via the projected connection port 1d. This occurs by connecting the supply liquid-side outlet port 4 and the dialysate inlet port 15c as well as the waste liquid-side inlet port 5 and the dialysate outlet port 15d, and also by connecting the supply liquid-side inlet port 3 and the projected connection port lb as well as the waste liquid-side outlet port 6 and the projected connection port 1c.

In the reciprocation pump, the supply liquid-side sub-pumping chamber P1a and the waste liquid-side sub-pumping chamber P2a are arranged, respectively, adjacent to the supply liquid-side pumping chamber P1 and the waste liquid-side pumping chamber P2 at their external side. Sealing members 12, 13 are arranged, respectively, in walls through which the rod 7 extends. The sealing member 12, 13 partition the supply liquid-side pumping chamber P1 and the supply liquid-side sub-pumping chamber P1a as well as the waste liquid-side pumping chamber P2 and the waste liquid-side sub-pumping chamber P2a. Thus, it is possible to prevent leakage of the dialysate to be supplied to the blood purification apparatus 15 as well as to prevent leakage of the waste dialysate from the blood purification apparatus 15 to the outside of the reciprocation pump.

In the reciprocation pump, the diaphragms 8, 9, respectively, are mounted on the distal end and the proximal end of the rod 7. The diaphragms 8, 9, with the casing 1, form the supply liquid-side sub-pumping chamber P1$a$ and the waste liquid-side sub-pumping chamber P2$a$, respectively. Thus, it is possible to eliminate the necessity of a separate sealing member at the mounting portions of the diaphragms. Furthermore, the dialysate is supplied to the blood purification apparatus 15 through both the supply liquid-side pumping chamber P1 and the supply liquid-side sub-pumping chamber P1$a$. The waste dialysate is discharged to the outside through both the waste liquid-side pumping chamber P2 and the waste liquid-side sub-pumping chamber P2$a$. Thus, it is possible to supply leaked dialysate to the blood purification apparatus 15 through the supply liquid-side sub-pumping chamber P1$a$ if the dialysate is leaked from the supply liquid-side pumping chamber P1 to the supply liquid-side sub-pumping chamber P1$a$ due to aged degradation of the sealing member 12. Similarly, it is possible to discharge the leaked waste dialysate from the waste liquid-side sub-pumping chamber P2$a$ to the outside if the waste dialysate leaks from the waste liquid-side pumping chamber P2 to the waste liquid -side sub-pumping chamber P2$a$.

A central sealing member 14 is arranged between the supply liquid-side pumping chamber P1 and the waste liquid-side pumping chamber P2 at substantially the reciprocating center of the plunger 2. The central sealing member 14 seals the supply liquid-side pumping chamber P1 from the waste liquid-side pumping chamber P2. Leaked dialysate can flow from the supply liquid-side pumping chamber P1 to the waste liquid-side pumping chamber P2. Leaked waste dialysate can flow from the waste liquid-side pumping chamber P2 to the supply liquid-side pumping chamber P1. Thus, it is possible to prevent the leaked dialysate and waste dialysate from leaking to the outside of the reciprocation pump.

Figure 5:
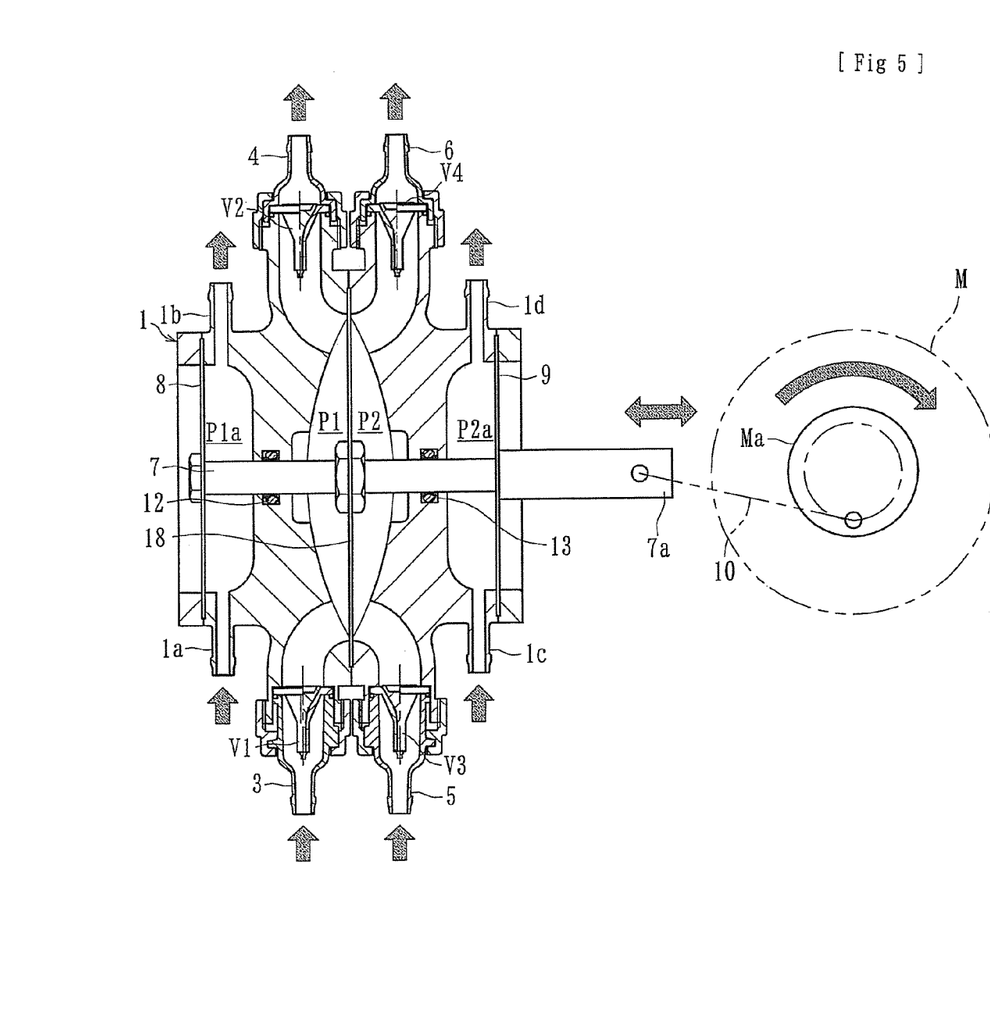
FIG. 5 is a longitudinal-section view of another embodiment of a reciprocation pump.

FIG. 5 shows another embodiment of the present disclosure. Here, a diaphragm 18 is in place of the plunger 2 mounted on the rod 7. The diaphragm 18, with the casing 1, forms the supply liquid-side pumping chamber P1 and the waste liquid side pumping chamber P2. Also in this embodiment, the supply liquid-side sub-pumping chamber P1$a$ and the waste liquid-side sub-pumping chamber P2$a$ are arranged, respectively, adjacent to the supply liquid-side pumping chamber P1 and the waste liquid-side pumping chamber P2 at their external side. Sealing members 12, 13 are arranged, respectively, in walls through which the rod 7 extends. The sealing members 12, 13 partition the supply liquid-side pumping chamber P1 and the supply liquid-side sub-pumping chamber P1$a$ as well as the waste liquid-side pumping chamber P2 and the waste liquid-side sub-pumping chamber P2$a$. Thus, it is possible to prevent leakage of the dialysate to be supplied to the blood purification apparatus 15 as well as to prevent leakage of the waste dialysate from the blood purification apparatus 15 to the outside of the reciprocation pump. Furthermore, in this embodiment, the reciprocation mechanism is formed by the diaphragm 18. Thus, it is possible to eliminate the central sealing member 14 for sealingly the supply liquid-side pumping chamber P1 and the waste liquid-side pumping chamber P2 as compared with a case using a plunger 2 for this purpose.

In the reciprocation pump, the connection arrangement between the reciprocation pump and the blood purification apparatus 15 is not limited to that shown in FIG. 4. Various connection arrangements can be adopted. Thus, if the connection arrangement is formed so that the dialysate can be supplied to the blood purification apparatus 15 through both the supply liquid-side pumping chamber P1 and the supply liquid-side sub-pumping chamber P1$a$. Also, the waste dialysate from the blood purification apparatus 15 is discharged to the outside through both the waste liquid-side pumping chamber P2 and the waste liquid-side sub-pumping chamber P2$a$. In addition, the sealing members 12, 13 and the central sealing member 14 may be other forms of sealing mechanisms other than an O-ring.

Furthermore, the present disclosure is not limited to a reciprocation pump used for supplying dialysate to a blood purification apparatus. It can be applied to other kinds of reciprocation pumps (whole industrial reciprocation pumps used for common use) that supply liquids to other objective apparatus other than the blood purification apparatus. In such a case, it is possible to prevent leakage of a liquid to be supplied to the objective apparatus as well as to prevent leakage of the waste liquid from the objective apparatus to the outside of the reciprocation pump. This occurs by arranging the supply liquid-side sub-pumping chamber and the waste liquid-side sub-pumping chamber, respectively, adjacent to the supply liquid-side pumping chamber and the waste liquid-side sub-pumping chamber at an external side. The sealing members, respectively, are arranged in walls through which the rod extends to partition the supply liquid-side pumping chamber and the supply liquid-side sub-pumping chamber as well as the waste liquid-side pumping chamber and the waste liquid-side sub-pumping chamber.

The present disclosure can be applied to a reciprocation pump and a dialysis apparatus equipped with such a reciprocation pump with a different external appearance from that shown in the accompanied drawings or having additional functions. The reciprocation pump includes a supply liquid-side sub-pumping chamber arranged adjacent to the supply liquid-side pumping chamber at the external side. A waste liquid-side sub-pumping chamber is arranged adjacent to the waste liquid-side pumping chamber at the external side. A rod extends through the supply liquid-side sub-pumping chamber, the supply liquid-side pumping chamber, the waste liquid-side pumping chamber and the waste liquid-side sub-pumping chamber. The rod is connected to the reciprocation mechanism and the driving source to transmit a driving force of the driving source to the reciprocation mechanism. Sealing members are arranged, respectively, in walls through which the rod extends to partition the supply liquid-side pumping chamber and the supply liquid-side sub-pumping chamber as well as the waste liquid-side pumping chamber and the waste liquid-side sub-pumping chamber.

The present disclosure has been described with reference to the preferred embodiment. Obviously, modifications and alternations will occur to those of ordinary skill in the art upon reading and understanding the preceding detailed description. It is intended that the present disclosure be construed as including all such alternations and modifications insofar as they come within the scope of the appended claims or their equivalents.

What is claimed is:

1. A reciprocation pump comprising:
   a supply liquid-side pumping chamber for supplying a liquid from a source to an objective apparatus;
   a waste liquid-side pumping chamber for discharging a waste liquid discharged from the objective apparatus to the outside;
   a reciprocation mechanism reciprocating between the supply liquid-side pumping chamber and the waste liquid-side pumping chamber, the reciprocating motion of the reciprocation mechanism performing suction and discharge of the liquid to and from the supply liquid-side pumping chamber as well as suction and discharge of the waste liquid to and from the waste liquid-side pumping chamber;

a driving source for driving the reciprocation mechanism;

the reciprocation pump with the supply liquid-side pumping chamber and the waste liquid-side pumping chamber adapted to supply the liquid from the source to the objective apparatus and to discharge the waste liquid from the objective apparatus to the outside;

a supply liquid-side sub-pumping chamber arranged adjacent to the supply liquid-side pumping chamber at an external side wherein liquid passes in series between the supply liquid-side chamber and the supply liquid-side sub-pumping chamber and into the objective apparatus;

a one way check valve between the supply liquid-side pumping chamber and the supply liquid-side sub-pumping chamber;

a waste liquid-side sub-pumping chamber arranged adjacent to the waste liquid-side pumping chamber at an external side wherein waste liquid passes in series between the waste liquid-side sub-pumping chamber and the waste liquid-side pumping chamber to discharge to the outside;

a one way check valve between the waste liquid-side pumping chamber and the waste liquid-side sub-pumping chamber;

a rod extending through the supply liquid-side sub-pumping chamber, the supply liquid-side pumping chamber, the waste liquid-side pumping chamber and the waste liquid-side sub-pumping chamber, the rod connected to the reciprocation mechanism and the driving source to transmit a driving force of the driving source to the reciprocation mechanism;

diaphragms, respectively, mounted on the distal end and the proximal end of the rod, the diaphragms form the supply liquid-side sub-pumping chamber and the waste liquid-side sub-pumping chamber, respectively, the diaphragms secured in a sealed manner by a peripheral edge fit into the reciprocating pump, the diaphragms displaced by the rod to vary the volume in their respective sub-pumping chamber; and sealing members arranged, respectively, in walls through which the rod extends to partition the supply liquid-side pumping chamber and the supply liquid-side sub-pumping chamber as well as the waste liquid-side pumping chamber and the waste liquid-side sub-pumping chamber.

2. The reciprocation pump of claim 1, wherein the liquid is supplied to the objective apparatus through both the supply liquid-side pumping chamber and the supply liquid-side sub-pumping chamber, and the waste liquid is discharged to the outside through both the waste liquid-side pumping chamber and the waste liquid-side sub-pumping chamber.

3. The reciprocation pump of claim 1, wherein the reciprocation mechanism comprises a plunger formed on the rod to form the supply liquid-side pumping chamber and the waste liquid-side pumping chamber, and a central sealing member is arranged between the supply liquid-side pumping chamber and the waste liquid-side pumping chamber at a position substantially at a reciprocating center of the plunger to seal the supply liquid-side pumping chamber from the waste liquid-side pumping chamber.

4. The reciprocation pump of claim 1, wherein the reciprocation mechanism comprises a diaphragm mounted on the rod to form the supply liquid-side pumping chamber and the waste liquid-side pumping chamber.

5. The reciprocation pump of claim 1, wherein the objective apparatus is a blood purification apparatus and the liquid is dialysate.

6. A dialysis apparatus equipped with the reciprocation pump of claim 5.

7. A reciprocation pump comprising:

a housing;

a supply liquid-side pumping chamber for supplying a liquid from a source to an objective apparatus, the supply liquid-side pumping chamber in the housing;

a waste liquid-side pumping chamber for discharging a waste liquid discharged from the objective apparatus to the outside, the waste liquid-side pumping chamber in the housing;

a reciprocation mechanism reciprocating between the supply liquid-side pumping chamber and the waste liquid-side pumping chamber in the housing, a member on the reciprocation mechanism in the housing separating the supply liquid side pumping chamber from the waste liquid side pumping chamber, the reciprocating motion of the reciprocation mechanism, via the member, performing suction and discharge of the liquid to and from the supply liquid-side pumping chamber as well as suction and discharge of the waste liquid to and from the waste liquid-side pumping chamber;

a driving source for driving the reciprocation mechanism;

the reciprocation pump with the supply liquid-side pumping chamber and the waste liquid-side pumping chamber adapted to supply the liquid from the source to the objective apparatus and to discharge the waste liquid from the objective apparatus to the outside;

a supply liquid-side sub-pumping chamber arranged in series with and adjacent to the supply liquid-side pumping chamber at an external side;

a waste liquid-side sub-pumping chamber arranged in series with and adjacent to the waste liquid-side sub-pumping chamber at an external side;

a one way check valve between the supply liquid-side pumping chamber and the supply liquid-side sub-pumping chamber;

a one way check valve between the waste liquid-side pumping chamber and the waste liquid-side sub-pumping chamber;

a rod extending through the supply liquid-side sub-pumping chamber, the supply liquid-side pumping chamber, the waste liquid-side pumping chamber and the waste liquid-side sub-pumping chamber, the rod connected to the reciprocation mechanism and the driving source to transmit a driving force of the driving source to the reciprocation mechanism;

diaphragms, respectively, mounted on the distal end and the proximal end of the rod, the diaphragms form the supply liquid-side sub-pumping chamber and the waste liquid-side sub-pumping chamber, respectively, the diaphragms secured in a sealed manner by a peripheral edge fit into the reciprocating pump, the diaphragms displaced by the rod to vary the volume in their respective sub-pumping chamber; and sealing members arranged, respectively, in walls through which the rod extends to partition the supply liquid-side pumping chamber and the supply liquid-side sub-pumping chamber as well as the waste liquid-side pumping chamber and the waste liquid-side sub-pumping chamber.

8. The reciprocation pump of claim 7, wherein the reciprocation member comprises a plunger formed on the rod to form the supply liquid-side pumping chamber and the waste liquid-side pumping chamber, and a central sealing member is arranged between the supply liquid-side pumping chamber and the waste liquid-side pumping chamber at a position substantially at a reciprocating center of the plunger to seal the supply liquid-side pumping chamber from the waste liquid-side pumping chamber.

* * * * *

UNITED STATES PATENT AND TRADEMARK OFFICE
CERTIFICATE OF CORRECTION

| | |
|---|---|
| PATENT NO. | : 9,885,348 B2 |
| APPLICATION NO. | : 13/479687 |
| DATED | : February 6, 2018 |
| INVENTOR(S) | : Hiroaki Suzuki |

Page 1 of 1

It is certified that error appears in the above-identified patent and that said Letters Patent is hereby corrected as shown below:

Column 2
Line 3            "motor Mon" should be --motor M--.

Column 4
Line 31           after "line", insert --III-III--.

Column 8
Line 52           "connection port lb" should be --connection port 1b--.

Signed and Sealed this
First Day of May, 2018

Andrei Iancu
*Director of the United States Patent and Trademark Office*